US010107920B2

(12) United States Patent
Danzer et al.

(10) Patent No.: US 10,107,920 B2
(45) Date of Patent: Oct. 23, 2018

(54) SENSOR BOARD FOR A DETECTOR MODULE

(71) Applicant: Siemens Aktiengesellschaft, München (DE)

(72) Inventors: Ludwig Danzer, Wendelstein (DE); Harald Geyer, Bubenreuth (DE); Miguel Labayen De Inza, Forchheim (DE); Jan Wrege, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 14/949,911

(22) Filed: Nov. 24, 2015

(65) Prior Publication Data

US 2016/0170032 A1 Jun. 16, 2016

(30) Foreign Application Priority Data

Dec. 10, 2014 (DE) ........................ 10 2014 225 396

(51) Int. Cl.
*G01T 1/00* (2006.01)
*H01L 31/115* (2006.01)
(Continued)

(52) U.S. Cl.
CPC ............ *G01T 1/00* (2013.01); *G01T 1/2018* (2013.01); *H01L 31/0203* (2013.01);
(Continued)

(58) Field of Classification Search
CPC .............................. G01T 1/00; H01L 31/0203
See application file for complete search history.

(56) References Cited

U.S. PATENT DOCUMENTS 4,521,689 A * 6/1985 Pritzkow ................. G01T 1/185
250/367
5,635,718 A * 6/1997 DePuydt ........... H01L 27/14634
250/208.1
(Continued)

FOREIGN PATENT DOCUMENTS

CN 1575423 A 2/2005
CN 101689556 A 3/2010
(Continued)

OTHER PUBLICATIONS

German Office Action dated Aug. 12, 2015.
(Continued)

*Primary Examiner* — Marcus Taningco
(74) *Attorney, Agent, or Firm* — Harness, Dickey & Pierce, PLC

(57) ABSTRACT

A sensor board for a detector module is disclosed. It includes, in a stack construction, at least one reader unit and a sensor layer arranged spaced from the reader unit in the direction of the stack. A gap formed by the spacing between the sensor layer and the reader unit is filled with a cured filling material such that at least one edge region of the sensor layer is free of the filling material. Furthermore, a method is disclosed for manufacturing a corresponding sensor board, and a detector module is disclosed for an X-ray detector having a number of sensor boards which are arranged to be mutually adjacent on a module carrier.

30 Claims, 8 Drawing Sheets

(51) Int. Cl.
  *G01T 1/20* (2006.01)
  *H01L 31/0203* (2014.01)
  *A61B 6/03* (2006.01)
  *A61B 6/00* (2006.01)

(52) U.S. Cl.
  CPC .............. *H01L 31/115* (2013.01); *A61B 6/03* (2013.01); *A61B 6/4208* (2013.01)

(56) References Cited

U.S. PATENT DOCUMENTS

| | | | | |
|---|---|---|---|---|
| 6,140,144 | A * | 10/2000 | Najafi | B81C 1/00269 438/106 |
| 7,807,010 | B2 * | 10/2010 | Pitault | H01L 23/544 156/285 |
| 7,902,976 | B2 * | 3/2011 | Doughty | G01T 1/026 250/370.1 |
| 8,759,784 | B2 * | 6/2014 | Prendergast | G01T 1/2907 250/370.1 |
| 2005/0092927 | A1 * | 5/2005 | Nagano | G01T 1/2928 250/370.11 |
| 2007/0181252 | A1 | 8/2007 | Bohm et al. | |
| 2009/0321013 | A1 | 12/2009 | Pitault | |
| 2010/0291726 | A1 | 11/2010 | Vieux | |
| 2012/0049079 | A1 * | 3/2012 | Yanoff | G01T 1/244 250/370.13 |
| 2012/0089180 | A1 * | 4/2012 | Fathi | B41J 2/17559 606/214 |
| 2012/0217593 | A1 * | 8/2012 | Graf | H01L 24/10 257/415 |
| 2013/0112882 | A1 | 5/2013 | Osawa | |
| 2013/0344654 | A1 * | 12/2013 | Limousin | H01L 24/11 438/108 |
| 2014/0284752 | A1 * | 9/2014 | Kalliopuska | H01L 27/14661 257/448 |

FOREIGN PATENT DOCUMENTS

| | | |
|---|---|---|
| DE | 102006001885 A1 | 7/2007 |
| DE | 102011079389 A1 | 1/2013 |
| DE | 102013207776 A1 | 10/2014 |
| FR | 2758654 B1 | 7/1998 |
| TW | 390032 B | 5/2000 |

OTHER PUBLICATIONS

Office Action for corresponding Chinese Application No. 201510903314.7 dated Feb. 9, 2018 and English translation thereof.

* cited by examiner

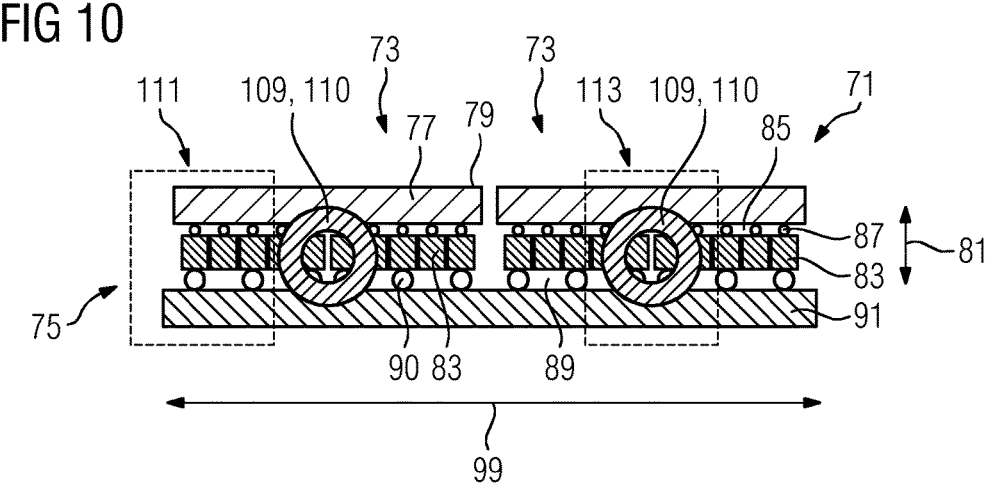
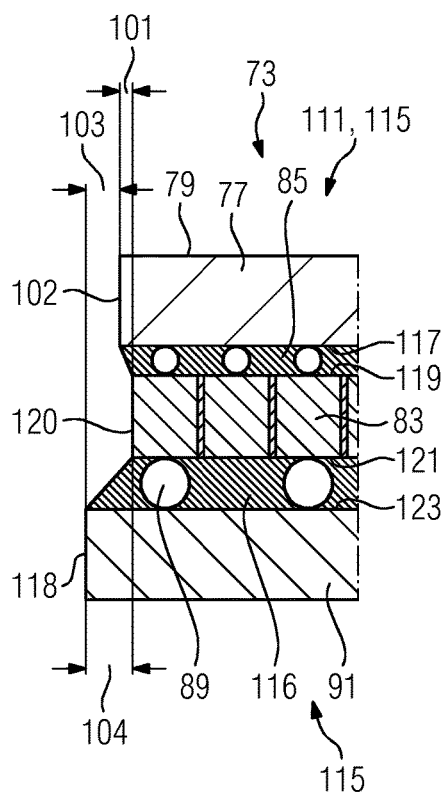
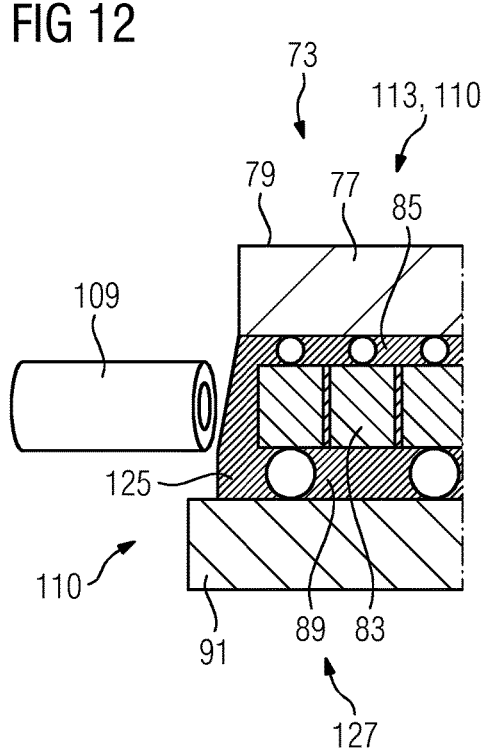

SENSOR BOARD FOR A DETECTOR MODULE

PRIORITY STATEMENT

The present application hereby claims priority under 35 U.S.C. § 119 to German patent application number DE 102014225396.9 filed Dec. 10, 2014, the entire contents of which are hereby incorporated herein by reference.

FIELD

At least one embodiment of the invention generally relates to a sensor board for a detector module. Further, at least one embodiment of the invention generally relates to a method for manufacturing a sensor board. Finally, at least one embodiment of the invention generally relates to a detector module having a number of accordingly manufactured sensor boards.

BACKGROUND

Within the context of high-resolution imaging methods, such as computer tomography in medical imaging, X-ray detectors are usually used to generate a high-resolution spatial image of an area of a patient under investigation.

In this context, an X-ray detector whereof the sensor layer takes the form of a directly converting semiconductor layer enables the quantitative and energy-selective detection of individual X-ray quanta. At the incidence of X-ray radiation, electron-hole pairs—that is to say pairs of negative and positive charge carriers—are generated in the sensor layer. As a result of voltage applied at the sensor layer or at the surface of the sensor layer, the charge carriers are separated and move towards the electrodes, or the surfaces of the sensor layer, of the respectively opposite charge. The current caused thereby, or a corresponding charge transfer, can be evaluated by downstream sensor electronics. Semiconductor materials in the form of CdTe, CdZnTe, CdTeSe, CdZnTeSe, CdMnTe, GaAs, Si or Ge that have a high absorption cross section for X-ray radiation are for example suitable for detecting X-ray quanta.

In particular in computer tomography, large-area X-ray detectors are required, and for this purpose a plurality of comparatively small detector modules are frequently used. Such detector modules in turn comprise individual sensor boards that are arranged adjacent to one another on a common module carrier at the smallest possible spacing (~100 µm) and whereof the sensor layers together form the sensor surface of a detector module.

Subdividing the sensor surface of a detector module by using mutually adjacent sensor boards enables, in particular, controlled scaling and, if the entire surface is used, also an increase in the signal yield of a detector. For this purpose, a sensor board usually includes a desired number of mutually adjacent hybrids arranged on a carrier. A hybrid itself comprises a sensor layer that is mounted on a certain number of reader units such as ASICs.

In the case of conventional scintillator-based sensor boards, the components are secured to one another in conventional manner by way of an adhesive procedure. For this, there is known from DE 10 2011 079 389 B4 a method (and analogously a device) that is suitable for filling, without overspill, a gap between a carrier and a component that is fixed to the carrier with an initially liquid adhesive. In the context of the method, which may be used for example when manufacturing detectors for the detection of X-ray and gamma radiation, such as in computer tomography equipment, an outlet aperture of a line connected to a reservoir is arranged at the peripheral edge of the gap.

The liquid adhesive in the reservoir then flows out of the outlet aperture directly into the gap and fills the latter, by way of capillary forces. The outlet aperture is only detached from the peripheral edge of the gap once the adhesive in the filled gap has cured and so can no longer flow, with the result that no material residue remains in the form of an overspill jutting beyond the peripheral edge of the filled gap.

In the case of quantum counting X-ray detectors, also called photon counting X-ray detectors, and the correspondingly used sensor boards, securing of the sensor layer on a respective number of reader units is usually performed by way of solder elements, so-called "bump bonds", by which the components to be connected are secured to one another. When manufacturing a hybrid for a sensor board of this kind, the solder elements are applied to the surface of the reader unit that faces the sensor layer in the assembled condition, and then the reader unit is brought into contact with the sensor layer by way of the solder elements. Subsequently heating the solder material connects the components to one another.

In a method of this kind, too, a gap is formed between the components that, for the purpose of improving mechanical stability and thermal conductivity between the components, has to be filled with an appropriate material, in particular an electrically insulating and thermally conductive material.

It is always a crucial challenge with a filling procedure of this kind, the so-called "underfill" procedure, to avoid material residues, caused by manufacture, on the peripheral edge of the manufactured sensor board or in general the components used in the context of manufacturing a sensor board.

In the context of filling, hitherto it has only been possible to make "classic" 1:1 hybrids each having one reader unit per sensor layer. Manufacture of so-called multi-hybrids (1:1, 1:2, 1:3 or 1:4 hybrids), which include a plurality of reader units per sensor layer, can only be performed by way of such a method at the expense of undesired impairment of the detector efficiency, since in this case material residues are formed in the intermediate edge regions of the components.

It is not possible to perform manufacture of sensor boards having a plurality of multi-hybrids (multi-hybrid sensor boards), since the gaps between the reader units of the hybrids also have to be filled with the filling material that is used. As a result, the individual sensor layers of the respective hybrids are coupled mechanically to one another, as a result of which the natural voltage of the sensor material is increased and thus the performance and efficiency of the respective X-ray detector is impaired.

SUMMARY

At least one embodiment of the invention is directed to a sensor board that may be manufactured in simplified manner by comparison with current sensor boards while ensuring that it functions unproblematically.

At least one embodiment of the invention is directed to a method for controlled filling of gaps in a sensor board which is simplified.

At least one embodiment of the invention is directed to a detector module having a number of corresponding sensor boards.

At least one embodiment of the invention is directed to a sensor board for a detector module, including in a stack construction at least one reader unit and a sensor layer that is arranged spaced from the reader unit in the direction of the stack, wherein the gap formed by the spacing between the sensor layer and the reader unit is filled with a cured filling material such that at least one edge region of the sensor layer is free of the filling material.

At least one embodiment according to the invention is directed to a method for manufacturing a sensor board according to one of the embodiments for a detector module, wherein the gap between the sensor layer and the reader unit is filled with a flowable that wets the surfaces delimiting the gap such that at least one edge region of the sensor layer remains free of the filling material.

Further preferred embodiments of the method become apparent from the subclaims relating to the sensor board. Here, the advantages mentioned for the sensor board may usefully be transferred to the method.

At least one embodiment of the invention is achieved by a detector module for an X-ray detector having a number of sensor boards which are arranged to be mutually adjacent on a module carrier, according to one of the embodiments described above.

Advantageously, the carrier of the or each detector module in the stack construction is connected, by way of the module carrier, to sensor electronics. For example, the data that is detected during X-ray image capture, that is to say the electrical signals from direct conversion of the X-ray radiation incident on a sensor surface, may be evaluated directly and used further. For this purpose, the sensor electronics may for example be read off in a corresponding evaluation routine.

Further preferred embodiments of the detector module become apparent from the subclaims relating to the sensor board. Here, the advantages mentioned for the sensor board may usefully be transferred to the detector module.

BRIEF DESCRIPTION OF THE DRAWINGS

Example embodiments of the invention are explained below in more detail with reference to a drawing, in which:

FIG. 10 shows the sensor board according to FIG. 7 in side view, FIG. 11 shows an enlarged detail of the edge region of the sensor board according to FIG. 10, with the gaps filled, FIG. 12 shows an enlarged detail of the intermediate region between two reader units of a hybrid of the sensor board according to FIG. 10, with the gaps filled.

DETAILED DESCRIPTION OF THE EXAMPLE EMBODIMENTS

Figure 1:
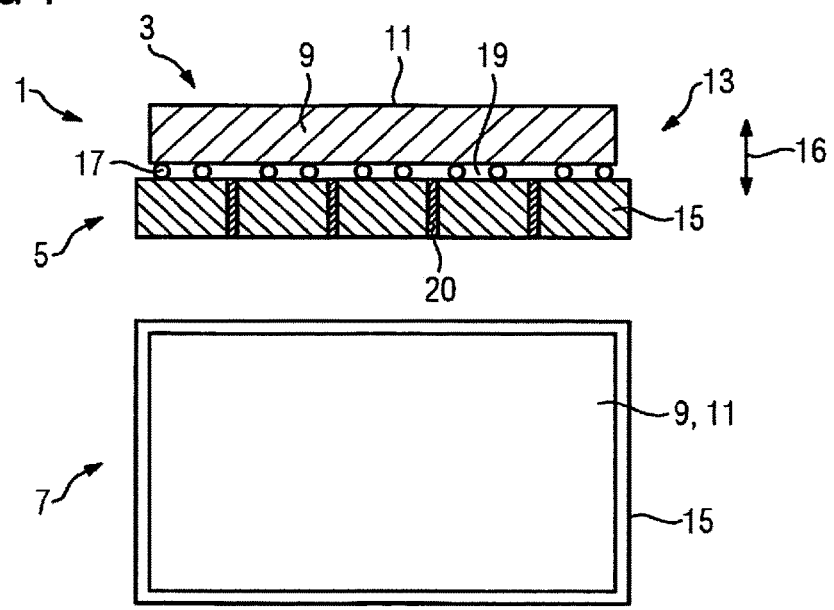
FIG. 1 shows a 1:1 hybrid according to the prior art, in side view and in plan view.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

At least one embodiment of the invention is directed to a sensor board for a detector module, including in a stack construction at least one reader unit and a sensor layer that is arranged spaced from the reader unit in the direction of the stack, wherein the gap formed by the spacing between the sensor layer and the reader unit is filled with a cured filling material such that at least one edge region of the sensor layer is free of the filling material.

At least one embodiment of the invention is based on the consideration that the gaps to be filled in the context of manufacturing a sensor board may be regarded as fine cavities, comparable with a capillary. A capillary may be filled with an appropriate liquid by utilizing the capillary effect, without applying an external pressure. The capillary effect is brought about by the surface tension of the liquid itself and the interfacial tension between the liquid and the fixed surface that is respectively in contact with the liquid (contact surface).

A precondition for the capillary effect is the wettability of the respective surface by the liquid that is used. Wettability is present when the adhesion forces between a liquid and the surface to be wetted are greater on the contact surface thereof than the cohesive forces within the liquid. In this case, a resulting force is produced at the contact surface that is directed out of the liquid and into the surface of the capillary. The liquid at the contact surface is "drawn" towards the latter to a certain extent and forms a concavely curved surface, that is to say a concave meniscus.

If these preconditions are fulfilled, it is possible in principle to use a flowable material to fill gaps produced between the respective components when manufacturing a sensor board, purely by utilizing the capillary effect. A wetting liquid forms a small contact angle on a corresponding surface. A non-wetting liquid does not cling to the surface or substrate; the result is a large contact angle.

However, depending on the geometry of the components and the size of the contact angle between the wetting liquid respectively used for filling a capillary and the surface, during capillary filling there may be an undesired outflow of liquid from the gap to be filled. The liquid, or the filling material used, goes beyond the edge of a capillary—that is to say the gap to be filled—and flows on outside the capillary, or is deposited there as a material residue.

When filling the gaps in a sensor board, it is important to suppress this effect in order to prevent undesired mechanical coupling of individual sensor layers and in particular to ensure that sensor boards to be arranged together on a module carrier can be placed side by side.

For this purpose, at least one embodiment the invention recognizes that it is possible to perform filling of gaps that is based on the capillary effect without undesired outflow of material from the corresponding gap if the material flow of the filling material is stopped in controlled manner during the filling such that it is possible to ensure that the or each edge region of the sensor layer is free of the filling material. The filling material does not flow out of the gap provided for receiving it; lateral covering of the sensor layer, that is to say the outflow of filling material from the gap, is avoided.

In order to ensure this, it is in particular advantageous if the geometry of the components used in a sensor board is changed by comparison with current geometries such that material flow out of the gap is stopped as a result of the geometric nature of the respective component.

In this context, it is fundamentally important that, if a liquid front comes to a component edge, the contact angle between the liquid and the surface changes abruptly at the component edge. If the change in the contact angle is large enough, the surface is no longer wetted and so further outflow of the material flow at this point is stopped.

In a particularly advantageous embodiment of the invention, the sensor layer has, in a longitudinal direction transverse to the stack direction, a dimension jutting beyond the reader unit. In the jutting region, the contact angle between the surface and the liquid increases during the filling procedure and the filling material is held in check at the opposite edge in the attempt overall to adopt a low-energy surface geometry. As a result of the change in contact angle, as described above, the filling material does not continue to flow out of the gap.

In other words, a small change in the component geometry—that is to say the provision of a dimension jutting from the sensor layer by comparison with the reader unit—can affect the material flow of a filling material that is used such that the formation of undesired residues at the peripheral edge of the sensor layer can be prevented, or at least reduced to a minimum that is acceptable from an engineering point of view.

Thus, a controlled and unproblematic filling by way of a filling material that can flow by capillary action can be achieved, in which the edge regions of the sensor material can be left uncovered in controlled manner. As desired, the solidified filling material will not jut beyond the edge of the sensor layer in the longitudinal direction.

An edge region of the sensor layer designates the side face of the sensor layer that extends in the stack direction. It is possible for only one edge region of the sensor layer, that is to say only one side face, to be free of the filling material. In particular, all the edge regions of the sensor layer, that is to say all the side faces of the sensor layer, are free of the filling material.

The edge regions include both the edge regions of a sensor layer that are part of the peripheral edge of a hybrid and the edge regions of sensor layers that are installed adjacent to one another in a hybrid (intermediate edge regions). In this way, on the one hand material residues are prevented from being produced at the peripheral edge and a desired ability to place them side by side is ensured. On the other hand, in particular when filling gaps in multi-hybrids, it is also possible to avoid filling gaps that extend between the sensor layers in the stack direction.

It is also advantageous if the gap produced as a result of the spacing between the sensor layer and the reader unit is filled with the cured filling material such that at least one edge region of the reader unit is free of the filling material. As already described in relation to the sensor layer, the at least one edge region of the reader unit designates the side face of the reader unit that extends in the stack direction, here too it being possible either for only one edge region or indeed all edge regions of the reader unit to be free of the filling material.

The filling material should be selected as a wetting liquid, in the broadest sense, in relation to the surfaces delimiting the gap to be filled, such that a sufficiently small contact angle is produced between the surface and the liquid or filling material. In general, the term "wetting liquid" is used when the contact angle is an acute angle. Accordingly, the material combinations of filling material and surface are advantageously selected such that a small contact angle is formed between the surface and the liquid.

The gap to be filled is made in the stack construction between the underside of the sensor layer and the upper side of the reader unit. The surfaces delimiting the gap between the reader unit and the sensor layer, that is to say the underside of the sensor layer and the upper side of the reader unit, are in the cured condition advantageously completely wetted by the filling material that is used, resulting in uniform filling of the gap.

To ensure sufficient wettability, preferably a filling material is used whereof the surface tension is smaller than the surface tension of the surfaces to be wetted, that is to say the surfaces facing the filling material. Particularly suitable filling materials are electrically insulating and thermally conductive materials.

On the basis of the capacity for capillary flow resulting from the surface tensions present, when a sensor board is manufactured the flowable filling material can be introduced without pressure into the gap between the components. Because of the capillary forces, the filling material flows into the gap. For this purpose, within the context of the filling procedure a filling device is advantageously arranged at the gap such that the flowable filling material fills the gap by itself. Accordingly, the term "without pressure" in the present document is understood to mean filling the gap purely on the basis of capillary forces, that is to say filling without applying an external pressure.

The filling material is preferably introduced into the gap by arranging the filling device at the peripheral edge of the hybrid. In the case of a multi-hybrid, that is to say for example in the case of a sensor layer arranged on four reader units (1:4 hybrid), it is possible to use a filling device that dispenses the filling material from the peripheral edge into the intermediate region between two mutually adjacent reader units. The use of a plurality of filling devices is also possible. As the filling device, needles or nozzles, which may be arranged at the respective position or positions on the peripheral edge, are for example suitable.

Before the gap is filled with filling material, the reader unit and the sensor layer are preferably fixed to one another in a stack construction by contact elements arranged between them in the stack direction. Preferably, balls of solder or solder bumps are used as the contact elements for fixing the components.

It is then a particularly simple matter, from an engineering point of view, to fill the gap between the sensor layer and the reader unit with an appropriate filling material without a residue if the dimension of the sensor layer jutting beyond the reader unit is 10 µm and 500 µm, in particular 50 µm and 100 µm.

Advantageously, a sensor board includes a certain number of hybrids that are arranged on a common carrier. Preferably, a reader unit (as part of a corresponding hybrid) is mounted on a carrier in a stack construction. The carrier, which is preferably a carrier ceramic, may be used as an intermediate substrate for transmitting signals from the reader unit to a corresponding electronics module, and serves to dissipate the heat produced in the sensor layer, in particular to a metal module carrier.

The reader unit and the carrier are advantageously arranged at a spacing from one another. The spacing, as seen in the stack direction, results from the contact elements that are used to secure the components to one another. For this purpose, balls of solder are preferably used.

In a furthermore advantageous embodiment of the invention, the gap produced by the spacing between the reader unit and the carrier is filled with a cured filling material. This filled gap is made, in the stack construction, between the underside of the reader unit and the upper side of the carrier. The surfaces delimiting the gap between the reader unit and the carrier are advantageously themselves completely filled with the filling material that is used.

In order to ensure that no undesired residues are produced in the edge region of the carrier even when the gap between the carrier and the reader unit is filled, the carrier preferably has a dimension jutting beyond the reader unit in the longitudinal direction. As a result of this jutting dimension, it is also possible in particular to fill the gap between the carrier and the reader unit such that at least one edge region of the carrier is free of the filling material.

As stated in relation to the sensor layer and the reader unit, the at least one edge region of the carrier designates the side face thereof that extends in the stack direction. In this case, either only one edge region or indeed all the edge regions, that is to say all the side faces of the carrier, may be free of the filling material.

For the filling material, in principle the same preferred developments apply here as were stated in relation to the filling material for the gap between the sensor layer and the reader unit. It is advantageous if the dimension of the carrier jutting beyond the reader unit is 0 µm and 5 000 µm, in particular 50 µm to 500 µm.

Preferably, the carrier also has a dimension jutting beyond the sensor layer in the longitudinal direction. The value of this jutting dimension is in this case advantageously determined from the difference in value of the dimension by which the carrier juts beyond the reader unit and the dimension by which the sensor layer juts beyond the reader unit.

As the filling material for the gap between the reader unit and the carrier, in this case advantageously the same filling material (flowable before it cures) is used as that used for filling the gap between the sensor layer and the reader unit. Thus, when the sensor board is manufactured, first all the required components (reader unit, sensor layer and carrier) are positioned in relation to one another and secured to one another, and then the filling material is applied at the same time to the gaps produced and fills them.

As the carrier, a carrier ceramic is preferably used. To ensure reliable securing by the filling material, good wetting of the carrier is required. The surface tension of the filling material here is preferably lower than the surface tension of the fixed surface, such that sufficient wetting of the upper side of the carrier, facing the gap, is ensured.

To prevent the gaps that extend in the stack direction, such as are present in multi-hybrids or multi-hybrid sensor boards, also from being filled during filling as a result of the capacity for capillary flow of the filling material, it is advantageous if the spacing between two reader units (of the respective hybrid) that are arranged on a carrier adjacent to one another in the longitudinal direction is in a range of between 100 µm and 1 000 µm, in particular between 200 µm and 500 µm.

With a spacing of this order of magnitude, even when there is a possibility that the filling material will flow out longitudinally, filling material can be prevented from coming into contact with itself from mutually adjacent gaps and, because of capillary force, from flowing as a joint stream of filling material into the gaps extending in the stack direction.

An alternative or additional possibility of preventing the gaps formed in the stack direction between the reader units of mutually adjacent hybrids from being filled is to adapt the geometry of the carrier used. For this purpose, the carrier geometry is preferably constructed such that it limits material flow into the gap or gaps.

In an advantageous embodiment of the invention, the carrier is constructed to have a step in the stack direction. A step of this kind stops flow of the filling material that is capable of capillary flow when the gaps are filled, and so effectively prevents the filling material from rising or creeping into the gaps between the reader units of hybrids that are arranged to be mutually adjacent on the carrier. In the assembled condition of a carrier serving as part of a sensor board, the step of the carrier advantageously extends in the stack direction between two mutually adjacent hybrids.

In a furthermore advantageous embodiment, a groove is made in the carrier. The groove fulfills the same purpose as a step, that is to say that it similarly serves to limit the material flow into the gaps between adjacent hybrids.

Further preferably, the reader unit and/or the sensor layer are provided in at least one of their edge regions with a coating. In this case, both the edge regions which face one another in the longitudinal direction, that is to say transversely to the stack direction (intermediate edge regions), may be provided with the coating. As an alternative or in addition, it is also possible for the edge regions formed at the peripheral edge to be provided with a coating. Preferably, as the coating material there may be used one with a lower surface tension than the surface tension of the filling material. In this way, the material flow may be interrupted early.

Further, the carrier may advantageously be provided with an at least partial coating—as an alternative or in addition to a coating that is applied to the reader unit and/or the sensor layer. In the assembled condition of the carrier, the coating is advantageously mounted on the carrier side facing the reader unit, between two mutually adjacent hybrids. The coating, both that of the carrier and that of the reader unit and/or sensor layer, may be for example a synthetic layer that is applied to the respective component as a thin film, passivation layer, dry film or mask.

Preferably, the sensor layer includes cadmium telluride (CdTe), cadmium zinc telluride (CdZnTe), cadmium zinc tellurium selenide (CdZnTeSe), cadmium tellurium selenide (CdTeSe), cadmium manganese telluride (CdMnTe), indium phosphide (InP), thallium bromide (TlBr2) or mercury iodide (HgI2). Semiconductor materials of this kind make it possible to directly convert the radiation incident thereon to an electrical signal, and are commercially available at good quality as regards charge transfer properties and homogeneity.

At least one embodiment according to the invention is directed to a method for manufacturing a sensor board according to one of the embodiments described above for a detector module, wherein the gap between the sensor layer and the reader unit is filled with a flowable that wets the surfaces delimiting the gap such that at least one edge region of the sensor layer remains free of the filling material.

Preferably, components that are of appropriate dimensions and construction are used for manufacturing a sensor board whereof the geometry permits filling of this kind. The filling takes place without pressure and by capillary action.

Advantageously, the gap between the reader unit and the carrier is also filled with a flowable filling material that wets the surfaces delimiting this gap such that at least one edge region of the carrier remains free of the filling material.

If, in a preferred embodiment, the dimension of the carrier in a longitudinal direction transverse to the stack direction also juts beyond the reader unit, then the material flow is also stopped when the gap between the reader unit and the carrier is filled by capillary action. Undesired material residues at the peripheral edge of the carrier are prevented from being formed.

The same applies accordingly to the or each edge region of the reader units. The gaps between the reader unit and the carrier, and between the reader unit and the sensor layer, are filled such that at least one edge region of the reader unit remains free of the filling material.

As a function of the number of hybrids used on each sensor board, and taking into account the sequence of positioning the hybrids on a carrier, the gaps may in principle be filled in different ways when a sensor board is manufactured.

On the one hand there is the possibility of first arranging the desired number of reader units on a sensor layer and filling the gaps that are produced. The hybrid that is manufactured in this way may then be mounted on a corresponding carrier, and the gap produced between the carrier and the reader unit of the hybrid also filled with the filling material by capillary action.

Particularly preferably, by way of the specified method, both the gap between the sensor layer and the reader unit and the gap between the reader unit and the carrier may be filled at the same time with the flowable filling material by capillary action. Here, first all the components are positioned and fixed on one another, and then a common filling procedure is carried out. In this way, the procedure of manufacturing a sensor board may be made significantly faster than current methods, and the costs of manufacture may be reduced.

The filling material is preferably introduced into the or each gap from at least one side face of the stack construction. For this purpose, a corresponding number of filling devices is preferably arranged on one side of the stack, at the peripheral edge of the hybrid or sensor board.

Further preferred embodiments of the method become apparent from the subclaims relating to the sensor board. Here, the advantages mentioned for the sensor board may usefully be transferred to the method.

At least one embodiment of the invention is achieved by a detector module for an X-ray detector having a number of sensor boards which are arranged to be mutually adjacent on a module carrier, according to one of the embodiments described above.

Advantageously, the carrier of the or each detector module in the stack construction is connected, by way of the module carrier, to sensor electronics. For example, the data that is detected during X-ray image capture, that is to say the electrical signals from direct conversion of the X-ray radiation incident on a sensor surface, may be evaluated directly and used further. For this purpose, the sensor electronics may for example be read off in a corresponding evaluation routine.

Further preferred embodiments of the detector module become apparent from the subclaims relating to the sensor board. Here, the advantages mentioned for the sensor board may usefully be transferred to the detector module.

FIG. 1 shows a 1:1 hybrid 3 that is known from the prior art and may be used in a sensor board 1, in side view 5 and in plan view 7. The hybrid 3 includes a sensor layer 9 having a sensor surface 11 that is arranged in a stack construction 13 on a reader unit 15. The arrangement is such that a spacing is created between the sensor layer 9 and the reader unit 15 in the stack direction 16.

Between the reader unit 15 and the sensor layer 9 there are arranged balls of solder 17 by way of which the components 9, 15 are fixed to one another at a spacing. The gap 19 that is produced by the spacing, between the reader unit 15 and the sensor layer 9, may be filled by capillary action by way of a suitable flowable filling material. For the purpose of making electrical contact with the sensor layer 9, through vias 20 (TSVs, through silicon vias) are introduced into the reader unit 15.

Figure 2:
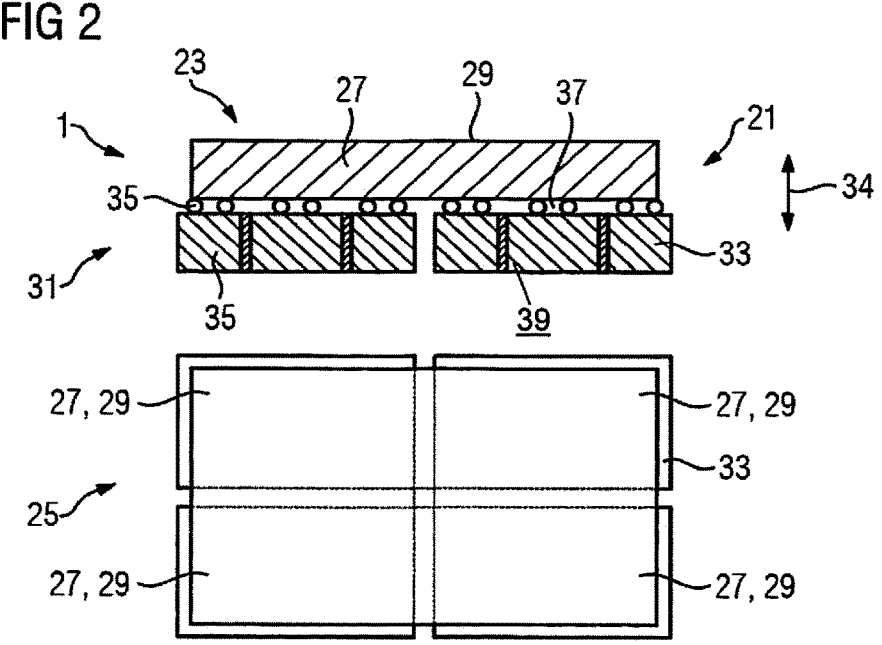
FIG. 2 shows a 1:4 hybrid according to the prior art, in side view and in plan view.

FIG. 2 also shows a hybrid 21 that is known from the prior art and may be installed in a sensor board 1, in a side view 23 and a plan view 25. This is a 1:4 hybrid having a sensor layer 27 and a sensor surface 29. The sensor layer 27 is mounted on four reader units 33, in a stack construction 31. The arrangement of the reader units 33 in relation to one another and their arrangement on the sensor layer 27 can be seen from the plan view 25.

As also in the case of the 1:1 hybrid from FIG. 1, balls of solder 35 are arranged between the reader units 33 and the sensor layer 27, for fixing the components 27, 33 in the stack direction 34, as a result of which a gap 37 is produced. The gap 37 may be closed off by being filled with a flowable filling material by capillary action. Again, electrical contact with the sensor layer 27 is made via through vias 39.

Figure 3:
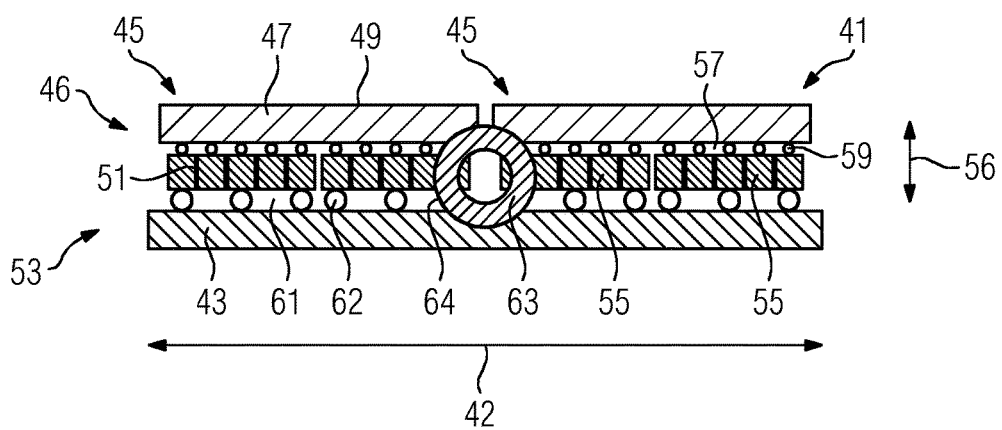
FIG. 3 shows a sensor board having two 1:2 hybrids arranged to be mutually adjacent on a carrier, in side view.

FIG. 3 shows, in a side view, a sensor board 41 having two 1:2 hybrids 45 that are arranged, adjacent to one another in a longitudinal direction 42 that is transverse to the stack direction 56, on a carrier 43 that takes the form of a carrier ceramic. This is therefore a multi-hybrid sensor board 41. The sensor board 41 can be installed in a detector module 46.

Each of the hybrids 45 of the sensor board 41 includes a respective sensor layer 47 having a sensor surface 49, wherein electrical contact is made with the sensor layer 47 via through vias 51. The sensor layers 47 are each spaced from these in the stack construction 53 and arranged on two reader units 55.

The spacing is the result of balls of solder 59, which are arranged between the reader units 55 and the sensor layers 47 in the stack direction 56 and by which the reader units 55 are each fixed to the corresponding sensor layer 47. As a result of the spacing, correspondingly fillable gaps 57 are produced between the reader units 55 and the sensor layers 47.

For arranging and fixing the hybrids 45 on the carrier ceramic 43, balls of solder 62 are also arranged in the gap 61 between the reader units 55 and the carrier 43.

Figure 4:
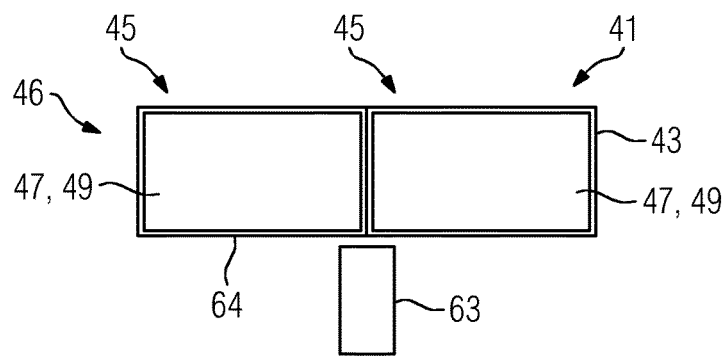
FIG. 4 shows the sensor board according to FIG. 3 in plan view, with a filling device arranged at the sensor board.

Furthermore, a filling device 63 in the form of a needle is shown, by which the gaps 57, 61 may be filled, without pressure, with a filling material that is capable of capillary flow. In the present case, the filling device 63 is arranged at the peripheral edge 64 of the sensor board 41, between the two hybrids 45. This arrangement of the needle 63 can clearly be seen from the plan view of the sensor board 41 in FIG. 4.

Figure 5:
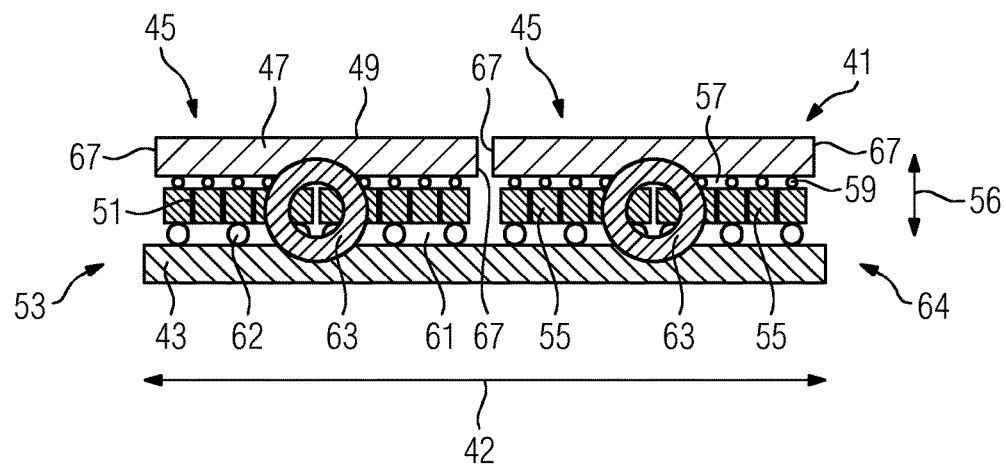
FIG. 5 shows the sensor board according to FIG. 3 in side view, having two filling devices arranged at the sensor board.
Figure 6:
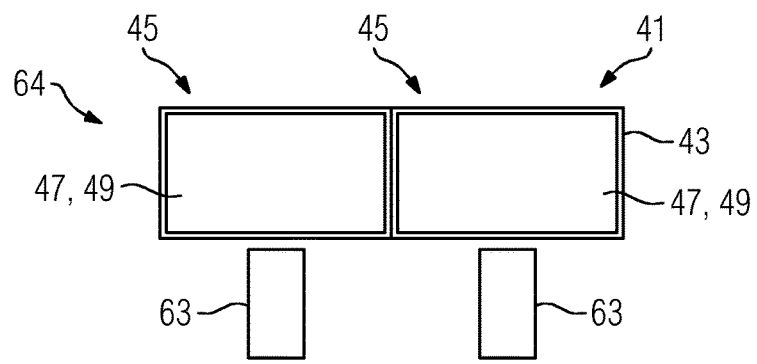
FIG. 6 shows the sensor board according to FIG. 3 in plan view, with the two filling devices arranged at the sensor board.

In FIGS. 5 and 6, the sensor board 41 from FIG. 3 is shown in a side view (FIG. 5) and a plan view (FIG. 6). The description of FIGS. 3 and 4 may be applied correspondingly to FIGS. 5 and 6. The difference consists in the arrangement of the filling device 63 used. According to FIGS. 5 and 6, two needles 63 are used which are respectively arranged between the adjacent reader units 55 of a hybrid 45.

In order to prevent material residues from being produced in the edge regions 67 of the sensor layers 47, that is to say on the side faces 67 extending in the stack direction 56, the sensor layers 47 have, in the installed condition, a dimension jutting beyond the reader units 55.

Figure 7:
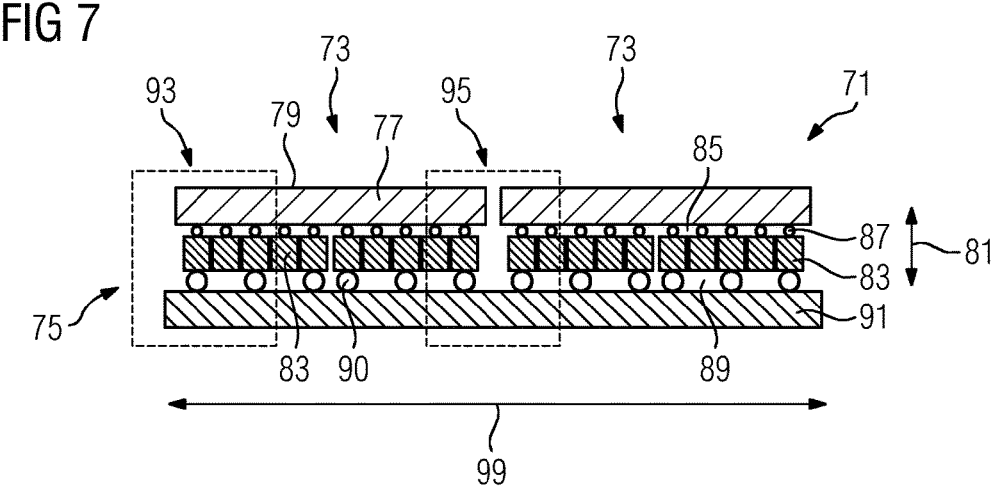
FIG. 7 shows a sensor board having four 1:4 hybrids, in side view.

These jutting dimensions become clear from the illustration according to FIGS. 7 to 9, which are described below. In FIG. 7, a further multi-hybrid sensor board 71 is shown. The sensor board 71 includes four 1:4 hybrids 73, of which only two hybrids 73 are visible because of the illustration from the side. Each hybrid 73 includes in the stack construction 75 a respective sensor layer 77 having a sensor surface 79. The sensor layer 77 is arranged, spaced therefrom in the stack direction 81, on four reader units 83. The spacing is the result of the balls of solder 87, which are arranged, as seen in the stack direction 81, in the gap 85 between the reader units 83 and the sensor layer 77 and by way of which the reader units 83 are respectively fixed to the corresponding sensor layer 77.

For their part, the reader units 83 of the four hybrids 73 are fixed by way of balls of solder 90 to a common ceramic carrier 91, forming gaps 89. All the gaps 85, 89 may be filled with a filling material at the same time in one procedure step.

Figure 8:
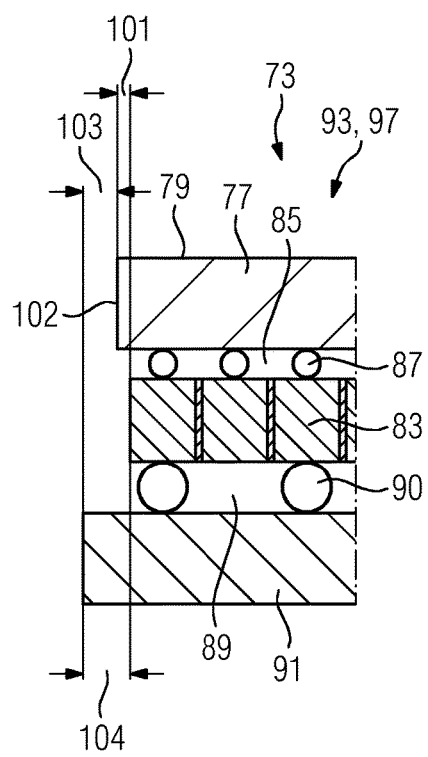
FIG. 8 shows an enlarged detail of the edge region of the sensor board according to FIG. 7.
Figure 9:
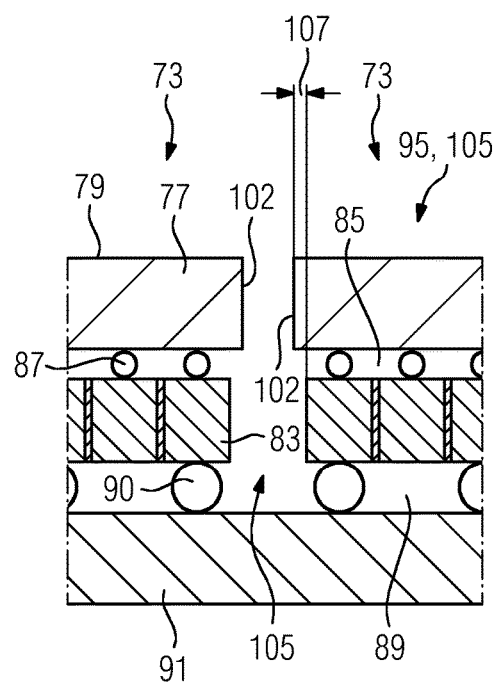
FIG. 9 shows an enlarged detail of the gap between two hybrids of the sensor board according to FIG. 7.

The details 93, 95 that are labeled in FIG. 7 are shown on a larger scale in FIGS. 8 and 9. The detail 93 according to FIG. 8 shows the enlarged peripheral edge region 97 of a hybrid 73 of the sensor board 71, and by way of this the dimensions or measurements of the reader units 83, the sensor layer 77 and the carrier 91 can be seen. In the present case, the sensor layer 77 has a dimension 101 jutting by 70 μm beyond the reader unit 83 in the longitudinal direction 99.

The jutting dimension 101 prevents a material overspill from being produced when the gap 89 is filled in the edge region 102 of the sensor layer 77 that is on the outside as seen in the longitudinal direction 99, that is to say at the side faces 102 extending in the stack direction 81. The dimension 103 by which the carrier 91 juts beyond the sensor layer 77 may be for example 100 μm. With a dimension 101 of 70 μm by which the sensor layer 77 juts beyond the reader unit 83, the dimension 104 by which the carrier 91 juts beyond the reader unit 83 is then 170 μm.

The detail 95 according to FIG. 9 shows an enlarged illustration of the gap 105 or intermediate region between two hybrids 73 of the sensor board 71. In this gap 105, the mutually adjacent sensor layers 77 also have a dimension 107 jutting by 70 μm beyond the reader units 83 in the longitudinal direction 99. When the gaps 85, 89 are filled, by way of these jutting dimensions 101, 103, 104, 107 it is possible to prevent the filling material from flowing in an uncontrolled manner, or creeping, and undesired material residues from being produced at the edge regions 102 of the sensor layers 77, that is to say at the mutually facing side faces 102 of the two sensor layers 77.

A possible arrangement of the filling devices 109 used for dispensing a filling material that flows by capillary action is shown in FIG. 10. Here, as also in FIG. 5, for filling the gaps 85, 89 of the sensor board 71, two filling devices 109 that take the form of needles are each arranged in intermediate regions 110 between the adjacent reader units 83 of a hybrid 73.

Furthermore, in FIG. 10 two details 111, 113 are labeled and are illustrated on a larger scale in FIGS. 11 and 12. The detail 111 according to FIG. 11 shows the enlarged peripheral edge region 115 of a hybrid 73 of the sensor board 71 according to FIG. 10, with the gaps 85, 89 filled. Starting from the filling devices 109 shown in FIG. 10, the electrically insulating and thermally conductive filling material 116 is introduced without pressure into the gaps 85, 89 between the components 77, 83, 91. During this, the filling material 116 flows into the gaps 85, 89 as a result of the capillary effect. In so doing, the filling material 116 wets the surface 117 of the sensor layer 77 that faces the reader unit 83 in the stack construction 75, that is to say the underside 117 of the sensor layer 77, the surface 119 facing the sensor layer 77 (upper side 119) and the surface 121 facing the carrier 91 (underside 121) of the reader unit 83, and the surface 123 facing the reader unit 83 in the stack construction 75 (upper side 123) of the carrier 91.

It can clearly be seen from the illustration according to FIG. 11 that, because of the dimension 101 of the sensor layer 77 jutting beyond the reader unit 83, and the dimension 103 of the carrier 91 jutting beyond the sensor layer 77 (or the dimension 104 of the carrier 91 jutting beyond the reader unit 83), no undesired material residues remain after filling at the edge region 102 of the sensor layer 77 or the edge region 118 of the carrier 91, that is to say at the side faces 118 of the carrier 91 extending in the stack direction 81.

The filling material 116 stops flowing by capillary action at the respective jutting dimensions 101, 103, 104 because of the change in contact angle. Accordingly, no material residue is to be found in the edge region 120 of the reader unit 83, that is to say at the side faces 120 of the reader units 83 extending in the stack direction 81, either.

FIG. 12 illustrates the detail 113 from FIG. 10, which shows the enlarged intermediate region 110 between the two hybrids 73 of the sensor board 71 with the filling device 109 arranged there. It can be seen from the illustration that there is a small material residue 125 at the position at which the filling device 109 is applied. This material residue 125 is unproblematic at this position, however, since in the present case this is the region 113 between two reader units 83. In this region 113, no impairment of the detector performance can be found if there is a material residue 125.

Figure 13:
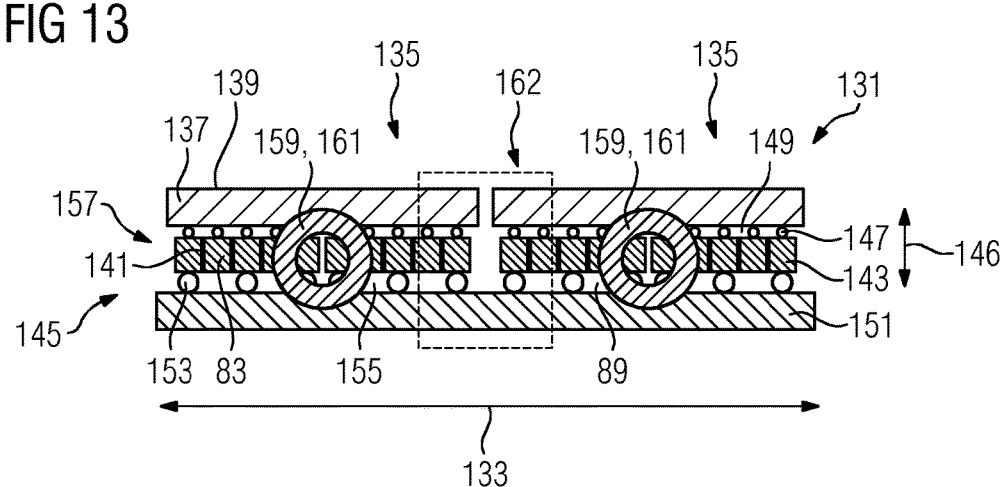
FIG. 13 shows a further sensor board having two 1:4 hybrids arranged to be mutually adjacent on a carrier, in side view.

In FIG. 13, a further sensor board 131, which is constructed to have two 1:4 hybrids 135 arranged mutually adjacent in the longitudinal direction 133, is shown in side view. Each of the two hybrids 135 includes a respective sensor layer 137 having a sensor surface 139, and electrical contact is made with these by way of through vias 141 in the reader units 143. The sensor layers 137 are arranged in a stack construction 145 on four reader units 143, of which only two reader units 143 are visible because of the illustration from the side.

The sensor layer 137 and the reader units 143 are respectively fixed to one another in the stack direction 146 by balls of solder 147. After the sensor board 131 has been assembled, the gaps 149 resulting from the spacing created by the balls of solder 147 are filled with a filling material that flows by capillary action.

Both hybrids 135 are arranged on a common carrier 151 and are also fixed by balls of solder 153. The resulting gaps 155 are also filled with a filling material that flows by capillary action. In this context, the gaps 149, 155 that are formed between the components 137, 143, 151 are filled in a common procedure step. For this purpose, two filling devices 161 that take the form of needles are arranged at the peripheral edge 157 of the sensor board 131, in each case at the intermediate regions 159 between the reader units 137 of the two hybrids 135.

Like the sensor board 71 according to FIGS. 10 to 12, the sensor layer 137 and the carrier 151 according to FIG. 13 each have a dimension jutting beyond the reader units 143. For reasons of clarity, these jutting dimensions are not drawn in. However, it goes without saying that the description relating to the sensor board 71 may be applied analogously to the sensor board 131.

Figure 14:
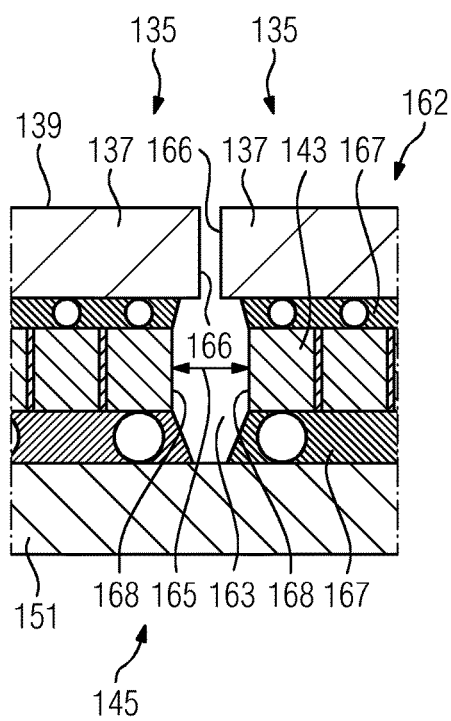
FIG. 14 shows an enlarged detail of the intermediate region between two hybrids of the sensor board according to FIG. 13, with the gaps filled.
Figure 15:
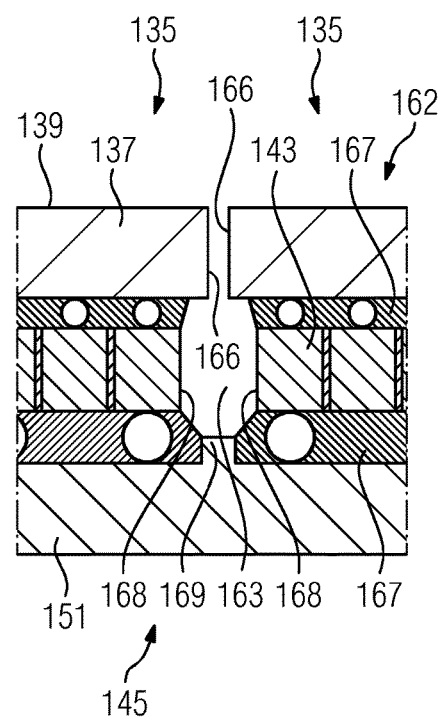
FIG. 15 shows the enlarged detail of the intermediate region according to FIG. 14, with the gaps filled and a carrier constructed to have a step.
Figure 16:
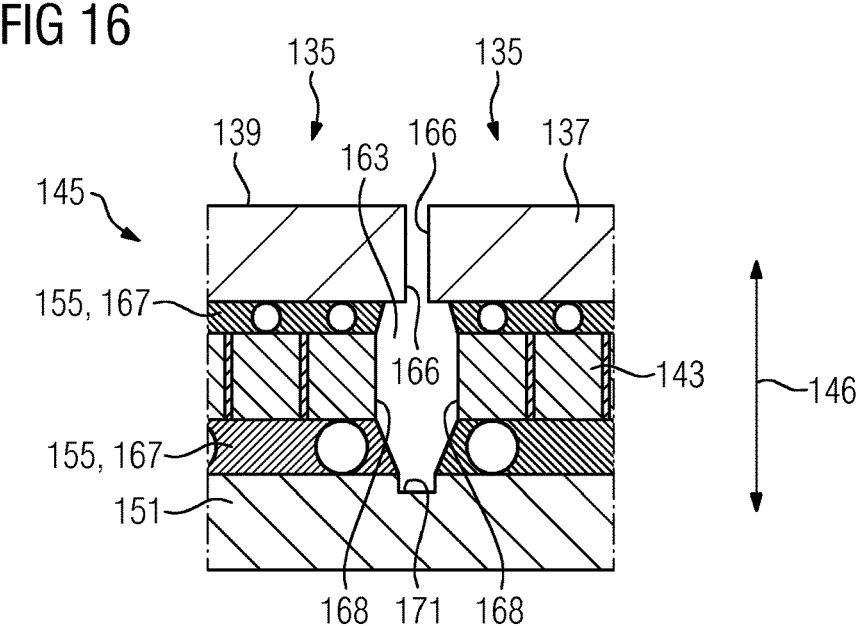
FIG. 16 shows the enlarged detail of the intermediate region according to FIG. 14, with the gaps filled and a carrier constructed to have a groove.

The detail 162 labeled in FIG. 13 is illustrated on a larger scale in FIGS. 14 to 16. The detail 162 shows the enlarged intermediate region 163 between the two hybrids 135. Here, each of the three FIGS. 14 to 16 shows a different way of preventing the undesired flow of material into the intermediate region 163 between the hybrids 135.

FIG. 14 shows the detail 162 of the sensor board 131 with an intermediate region 163 in which the spacing 165 between the two reader units 143 of the respective hybrids 135, which are arranged adjacent in the longitudinal direction 133 on the carrier 151, is 220 μm. In this way, it is possible to prevent the filling material 167 from flowing into the intermediate regions or gaps 163 between the hybrids 135 and extending into the gap 163 in the stack direction 146.

Accordingly, the gaps 155 between the components may be filled such that both the edge region 166 of the sensor layers 137 and also the edge region 168 of the reader units 143 are free of the filling material 167. In other words, the side faces 166 of the sensor layers 137 that extend in the stack direction 146, and the side faces 168 of the reader units that extend in the stack direction 146, are free of the filling material 167.

In FIG. 15, the carrier 151 is formed with a step 169 in the stack direction 146 in the gap 163. A step 169 of this kind also stops the flow of filling material 167 that flows by capillary action, and so effectively stops the flow thereof into the gaps 163 between the hybrids 135. Because the contact angle changes when the filling material 167 reaches the step 169, the step 169 prevents material residues from being produced in the edge regions 166, 168.

FIG. 16 shows the carrier 151 with a groove 171 made in the intermediate region 163. Here, the groove 171 fulfills the same purpose as the step 169 according to FIG. 15: it limits the flow of material into the gaps 163 between the hybrids 135. In this case too, filling of the gaps 155 may be performed as a result of the change in contact angle brought about by the groove such that both the edge region 166 of the sensor layers 137, that is to say their side face 166, and also the edge region 168 of the reader units 143, that is to say their side face 168, are free of the filling material 167.

Figure 17:
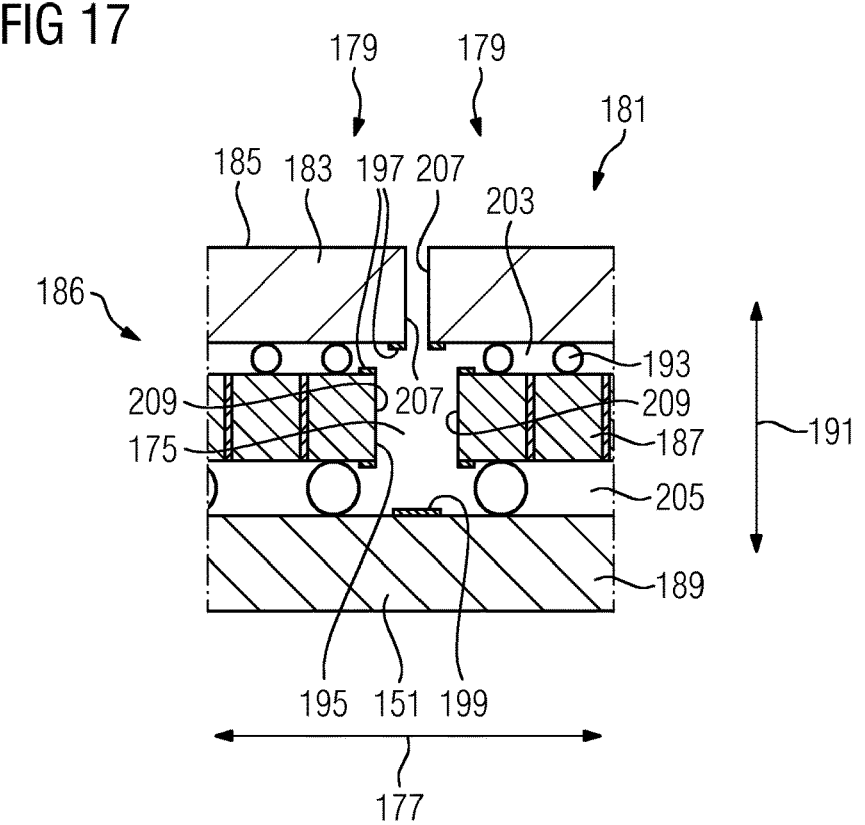
FIG. 17 shows the enlarged detail of the intermediate region according to FIG. 13, with the intermediate regions unfilled and a coating applied to the components.
Figure 18:
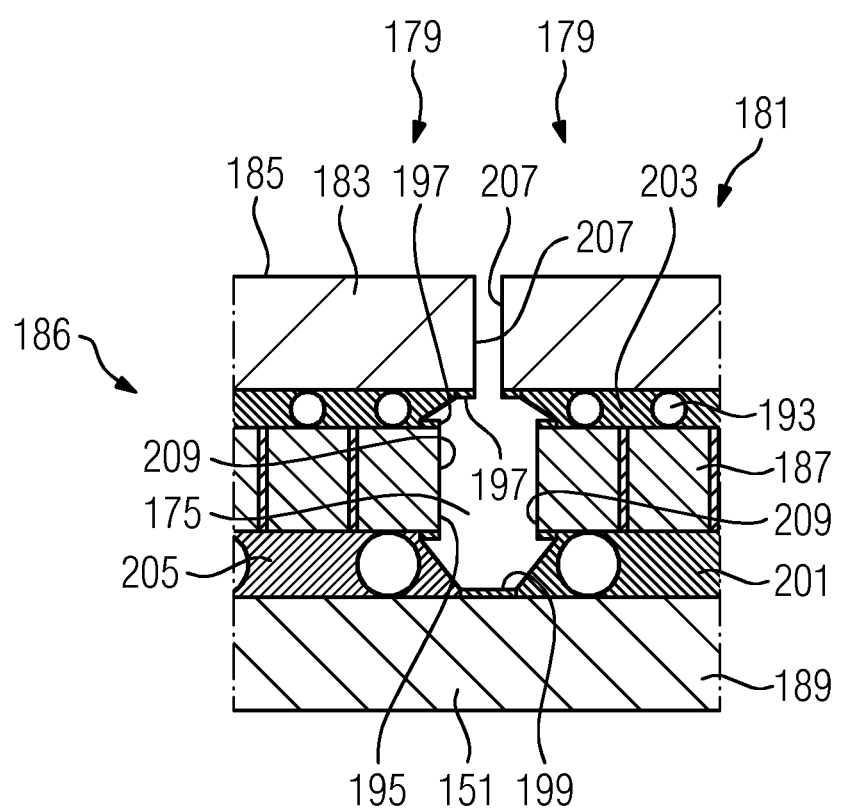
FIG. 18 shows the detail according to FIG. 17 with the intermediate regions filled.

FIGS. 17 and 18 show the gap 175, or the intermediate region, between two 1:2 hybrids 179, mutually adjacent in the longitudinal direction 177, of a further sensor board 181 in the unfilled condition (FIG. 17) and the filled condition (FIG. 18).

Both hybrids 179 also include a respective sensor layer 183 having a sensor surface 185. In the stack construction 186, each sensor layer 183 is arranged on in each case two reader units 187. The hybrids 179 are arranged on a common carrier 189. The sensor layers 183 are each spaced in the stack direction 191 from the reader units 187 by balls of solder 193. The same applies to the spacing of the reader units 187 from the carrier 189. In this case too, balls of solder are used 194.

In the present case, the reader units 187 and the sensor layers 183 are provided in their mutually facing edge regions 195 with a coating 197. In the present case, as the coating material a thin synthetic film having a low surface tension is used. The carrier 189 is also provided with a coating 199 of this kind. In the present case, the coatings 197, 199 are applied to the surfaces of the reader units 187 and sensor layers 183 that delimit the gaps 203, 205. The coating 199 of the carrier 189 is, in the present case, applied in the intermediate region 175 between the two hybrids 179, also as a thin coating on the surface of the carrier 189 facing the reader units 187 thereon.

The coatings 197, 199 have a critical surface tension that is lower than the surface tension of the filling material 201 that is used, such that the material flow of the filling material 201 that is drawn into the gaps 203, 205 is stopped on reaching the coating 197, 199 because of the relatively poor wettability of the coating 197, 199. In this way, an undesired flow of material into the gap 175 between the mutually adjacent hybrids 179 can be prevented. Accordingly, with a coating 197, 199 too it is possible to ensure a filling procedure in which the edge regions 207 of the sensor layers 183, forming side faces, and the edge regions 209 of the reader units 187, forming side faces, remain free of the filling material 201. This can be seen in FIG. 18.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, etc. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A sensor board for a detector module, in a stack construction, comprising:
   at least one reader unit; and
   a plurality of sensor layers, each of the plurality of sensor layers arranged spaced from a respective at least one reader unit in a direction of the stack of the stack construction, the sensor layer including a first surface and an opposing second surface;
   a filling material on an entirety of one of the first surface or the opposing second surface, and
   a carrier in the stack construction;
   wherein the each sensor layer and the respective at least one reader unit are separated from each other by a first spacing, the first spacing including the filling material such that at least one edge surface of the sensor layer is free of the filling material;
   wherein respective edge surfaces of each of the plurality of sensor layers are separated from each other by a second spacing, the second spacing being free of the filling material; and
   wherein the carrier includes a groove that is free of filling material and is configured to prevent the filling material from entering gaps between adjacent reader units of hybrids on the carrier.

2. The sensor board of claim 1, wherein the first spacing is filled with the filling material such that a respective edge region of the at least one reader unit is free of the filling material.

3. The sensor board of claim 2, wherein surfaces delimiting the filled first spacing between the at least one reader unit and the sensor layer are completely wetted by the filling material.

4. The sensor board of claim 1, wherein the sensor layer includes in at least one edge region, in a longitudinal direction transverse to the stack direction, a dimension jutting beyond the at least one reader unit.

5. The sensor board of claim 4, wherein the dimension of the sensor layer jutting beyond the at least one reader unit is 50 μm to 100 μm.

6. The sensor board of claim 4, wherein surfaces delimiting the filled first spacing between the at least one reader unit and the sensor layer are completely wetted by the filling material.

7. The sensor board of claim 6, wherein the dimension of the sensor layer jutting beyond the at least one reader unit is between 50 μm to 100 μm.

8. The sensor board of claim 1, wherein surfaces delimiting the filled first spacing between the at least one reader unit and the sensor layer are completely wetted by the filling material.

9. The sensor board of claim 1,
wherein the at least one reader unit is mounted on the carrier in the stack construction.

10. The sensor board of claim 9, wherein the at least one reader unit and the carrier are arranged at a third spacing from one another in the stack direction.

11. The sensor board of claim 10, wherein the third spacing between the at least one reader unit and the carrier is filled with the filling material such that at least one edge region of the carrier is free of the filling material.

12. The sensor board of claim 10, wherein the third spacing between the at least one reader unit and the carrier is filled with the filling material such that at least one edge region of the at least one reader unit is free of the filling material.

13. The sensor board of claim 10, wherein surfaces delimiting the third spacing between the at least one reader unit and the carrier are completely wetted by the filling material.

14. The sensor board of claim 9, wherein the carrier has, in a longitudinal direction transverse to the stack direction and in at least one edge region, a dimension jutting beyond the at least one reader unit.

15. The sensor board of claim 14, wherein the dimension of the carrier jutting beyond the at least one reader unit is between 0 μm and 5000 μm.

16. The sensor board of claim 15, wherein the dimension of the carrier jutting beyond the at least one reader unit is between 50 μm to 500 μm.

17. The sensor board of claim 14, wherein the at least one reader unit includes at least two reader units and wherein a fourth spacing between the at least two reader units arranged on the carrier adjacent to one another in the longitudinal direction is between 100 μm and 1000 μm.

18. The sensor board of claim 17, wherein the at least one reader unit includes at least two reader units and wherein a spacing between two reader units arranged on a carrier adjacent to one another in the longitudinal direction is between 200 μm and 500 μm.

19. A detector module for an X-ray detector comprising:
a plurality of sensor boards arranged to be mutually adjacent on a module carrier, each of the sensor boards being the sensor board of claim 14.

20. The sensor board of claim 9, wherein the carrier is provided with an at least partial coating.

21. A detector module for an X-ray detector comprising:
a plurality of sensor boards arranged to be mutually adjacent on a module carrier, each of the sensor boards being the sensor board of claim 9.

22. The sensor board of claim 1, wherein at least one of the at least one reader unit and the sensor layer is provided, in at least one edge region, with a coating.

23. A detector module for an X-ray detector comprising:
a plurality of sensor boards arranged to be mutually adjacent on a module carrier, each of the sensor boards being the sensor board of claim 1.

24. The sensor board of claim 1, wherein the at least one reader unit and one of the plurality of sensor layers forms a hybrid and facing edge surfaces of each reader unit of respective hybrids are separated from each other by a fourth spacing, the fourth spacing being free of the filling material.

25. A method for manufacturing a sensor board for a detector module, comprising:
filling a first spacing, between one of a plurality of sensor layers and at least one respective reader unit of the sensor board, with a flowable filling material that wets an entirety of surfaces delimiting the first spacing such that a respective edge surface of the sensor layer remains free of the flowable filling material, each of the plurality of sensor layers having a first sensor surface and an opposing second sensor surface, the first and second surfaces delimiting the first spacing including the first sensor surface and a reader surface;
applying the filling material to one of the first sensor surface and the second sensor surface; and
arranging the at least one reader unit in a stack construction at a spacing therefrom on a carrier, a third spacing defined by a carrier surface and one of a first reader surface and a second reader surface;
wherein a respective edge surface of each of the plurality of sensor layers is separated from an edge surface of an adjoining sensor layer by a second spacing, the second spacing being free of the filling material; and
wherein the carrier includes a groove that is configured to prevent the filling material from entering gaps between adjacent reader units of hybrids on the carrier.

26. The method of claim 25, further comprising:
filling the third spacing with a flowable filling material that wets surfaces delimiting the third spacing such that at least one edge surface of the carrier remains free of the flowable filling material.

27. The method of claim 26, further comprising:
filling both the first spacing and the third spacing at the same time with the flowable filling material.

28. The method of claim 27, wherein the flowable filling material is introduced into at least one of the first spacing and the third spacing from at least one side face of the stack construction.

29. The method of claim 26, further comprising:
introducing the flowable filling material into at least one of the first spacing and the third spacing from at least one side face of the stack construction.

30. The method of claim 25, wherein the at least one reader unit and one of the plurality of sensor layers forms a hybrid and facing edge surfaces of each reader unit of respective hybrids are separated from each other by a fourth spacing, the fourth spacing being free of the filling material.

* * * * *